US00PP21967P2

(12) United States Plant Patent
Kubik

(10) Patent No.: US PP21,967 P2
(45) Date of Patent: Jun. 7, 2011

(54) ***THUJA* PLANT NAMED 'JANED GOLD'**

(50) Latin Name: *Thuja occidentalis*
Varietal Denomination: Janed Gold

(76) Inventor: Edward Kubik, Janowice (PL)

( * ) Notice: Subject to any disclaimer, the term of this patent is extended or adjusted under 35 U.S.C. 154(b) by 0 days.

(21) Appl. No.: 12/798,373

(22) Filed: Mar. 31, 2010

Related U.S. Application Data

(60) Provisional application No. 61/211,933, filed on Apr. 6, 2009.

(51) Int. Cl.
*A01H 5/00* (2006.01)

(52) U.S. Cl. ..... Plt./213

(58) Field of Classification Search ..... Plt./213
See application file for complete search history.

*Primary Examiner* — Annette Para

(57) ABSTRACT

A new and distinct cultivar of *THUJA* plant named 'JANED GOLD' that is dense and uniform in growth habit, becoming conical with age, and bearing bright yellow-gold foliage year round. In combination these characteristics set 'JANED GOLD' apart from all other existing varieties of *THUJA* known to the inventor.

3 Drawing Sheets

Genus: *THUJA*.
Species: *occidentalis*.
Denomination: 'JANED GOLD'.

BACKGROUND OF THE INVENTION

The present invention relates to a new and distinct cultivar of *THUJA* plant, commonly known as Eastern arborvitae or white cedar. The new cultivar is known botanically as *THUJA occidentalis* and will be referred to hereinafter by the cultivar name 'JANED GOLD'. 'JANED GOLD' may be grown as a specimen plant or as a hedging plant, and may be left unpruned or may be pruned into a formal shape or hedge.

'JANED GOLD' was discovered by the inventor in 1999 as a naturally occurring chance seedling within a commercial crop of the green foliaged variety of *Thuja occidentalis* named 'Smaragd' (unpatented). The discovery took place at the inventor's nursery in Janowice, Poland. 'Smaragd', which originated in Denmark, is commonly sold in the United States under the alternate trade names "Emerald" or "Emerald Green". Emerald is the English translation of the Danish word smaragd. Unlike 'Smaragd' whose foliage is green throughout all stages of growth, the inventor noticed that the chance seedling, 'JANED GOLD', exhibited bright yellow-gold foliage.

The closest known comparison plant known to the inventor is the parent variety *Thuja occidentalis* 'Smaragd'. 'JANED GOLD' is distinguishable from the comparison plant by foliage color as above and by growth rate. During its first three years 'JANED GOLD' grows at a slightly slower rate than 'Smaragd' then after three years both growth rates are comparable.

'JANED GOLD' is an evergreen shrub that exhibits bright yellow-gold foliage color year round. The growth habit of 'JANED GOLD' is dense and upright. Plants of 'JANED GOLD' become conical in shape with age. Crowded horizontal branchlets spread into flattened sprays.

In common with the parent variety 'Smaragd', 'JANED GOLD' tolerates a wide range of climatic conditions and has been found to survive without injury in temperatures equivalent to USDA Hardiness Zone 5. Testing for hardiness continues in colder zones. 'JANED GOLD' tolerates growing in full sunlight which intensifies the yellow-gold coloration of the foliage. However, the yellow-gold foliage is present and is distinct from 'Smaragd' in all conditions of light intensity.

'JANED GOLD', was first asexually propagated by the inventor in 2000 at the inventor's nursery in Janowice, Poland. Asexual propagation was accomplished using hardwood cuttings. Since that time, under careful observation, the distinguishing characteristics of 'JANED GOLD' have been determined stable, uniform, and to reproduce true to type in successive generations of asexual reproduction.

Applications for grants of Plant Breeders Rights have been filed for 'JANED GOLD' in Poland (Application Number O 1661, filing date December 14, 2006) and in The European Community (Application Number 2008/1194. filing date May 28, 2008).

Except for the inventor's submission of 'JANED GOLD' into the new varieties competition at the Polish Nurserymen's Association trade show in August 2008, the inventor retained possession and control of all plants of 'JANED GOLD' until April 2009 when the first plants of 'JANED GOLD' were made available to the public.

SUMMARY OF THE INVENTION

The distinguishing characteristics of 'JANED GOLD' are as follows. In combination these traits set 'JANED GOLD' apart from all other existing varieties of *THUJA* known to the inventor. 'JANED GOLD' has not been tested under all possible conditions and phenotypic differences may be observed with variations in environmental, climatic and cultural conditions, however, without any variance in genotype.

1. The growth habit of 'JANED GOLD' is dense, uniform, and narrow upright, becoming conical with age.
2. 'JANED GOLD' is robust and wind resistant.
3. 'JANED GOLD' is hardy at least in temperatures of minus 20° Celsius.
4. The color of the foliage of 'JANED GOLD' is bright yellow-gold in all seasons of the year.
5. 'JANED GOLD' achieves a height of 17 cm. in its first year of growth, and a height of approximately 2.5 meters after ten years of growth.

BRIEF DESCRIPTION OF THE DRAWINGS

The accompanying color drawings illustrate the overall appearance of 'JANED GOLD' showing the colors of its foliage as true as it is reasonably possible to obtain in color reproductions of this type.

The drawing labeled as FIG. 1 depicts a plant of 'JANED GOLD' which is 3 years 6 months of age and which has been growing out of doors in Janowice, Poland.

Figure 1:
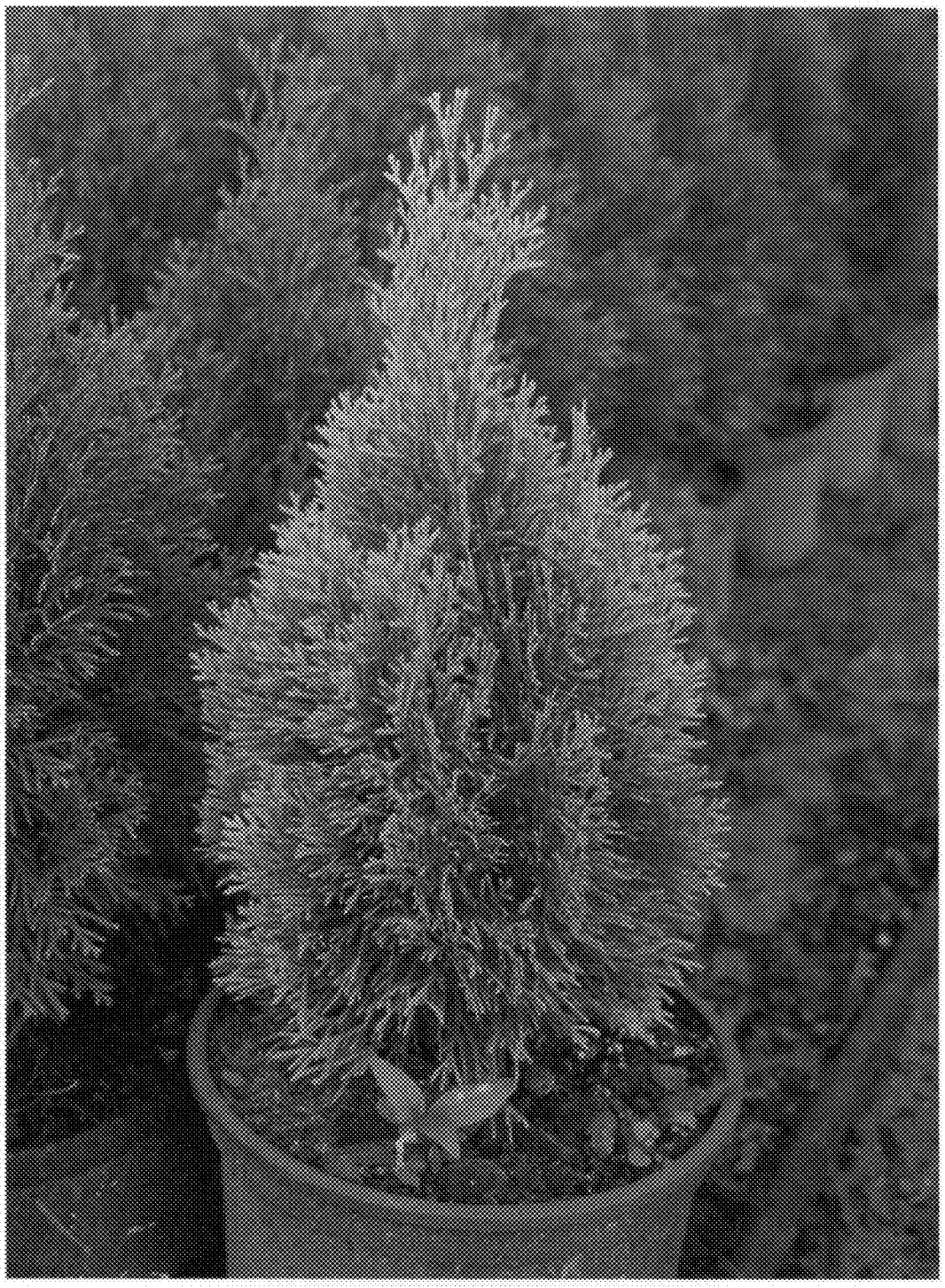
Figure 2:
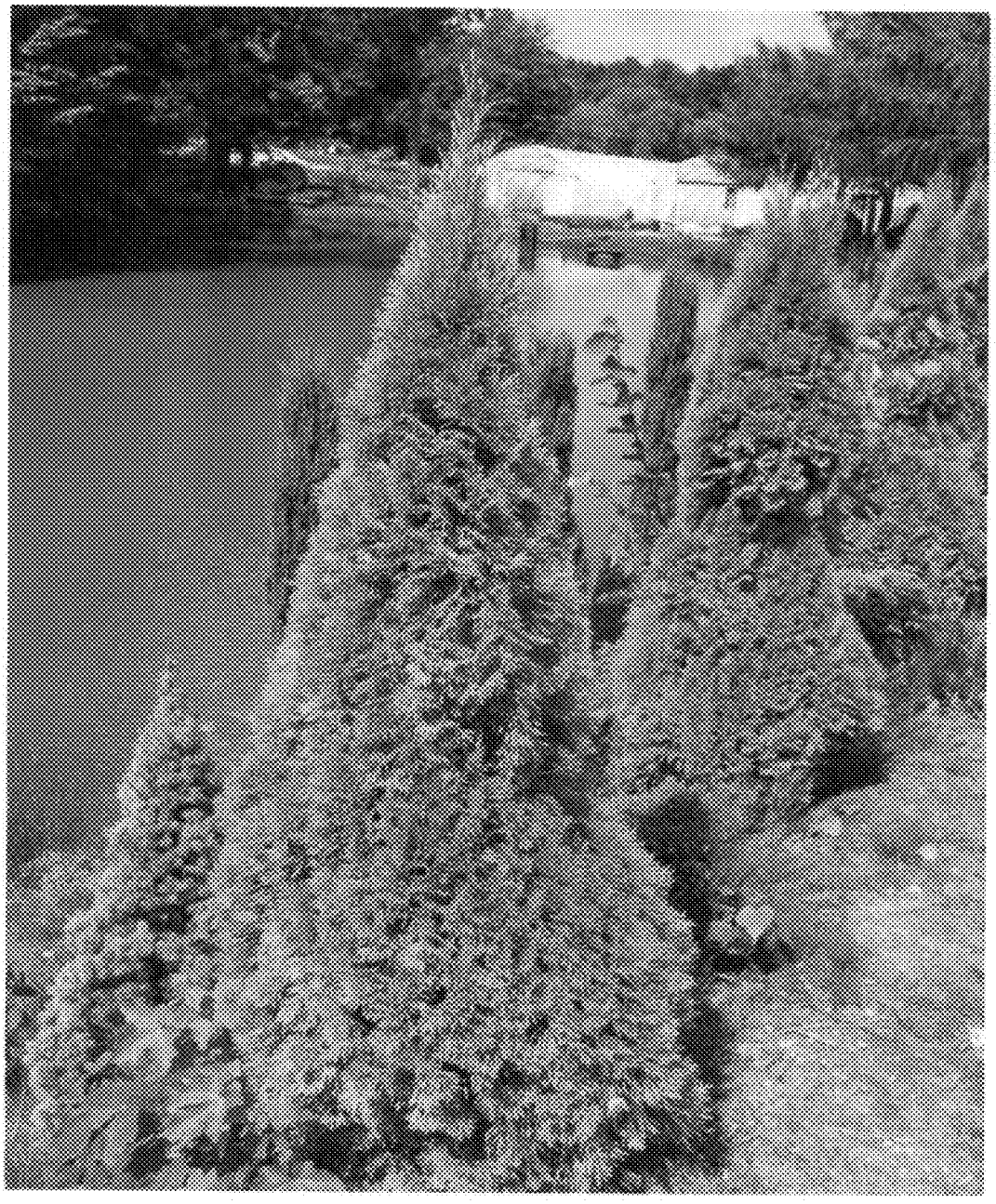

The drawing labeled as FIG. 2 depicts a plant of 'JANED GOLD' which is 10 years of age and which has been growing out of doors in Janice, Poland.

Figure 3:
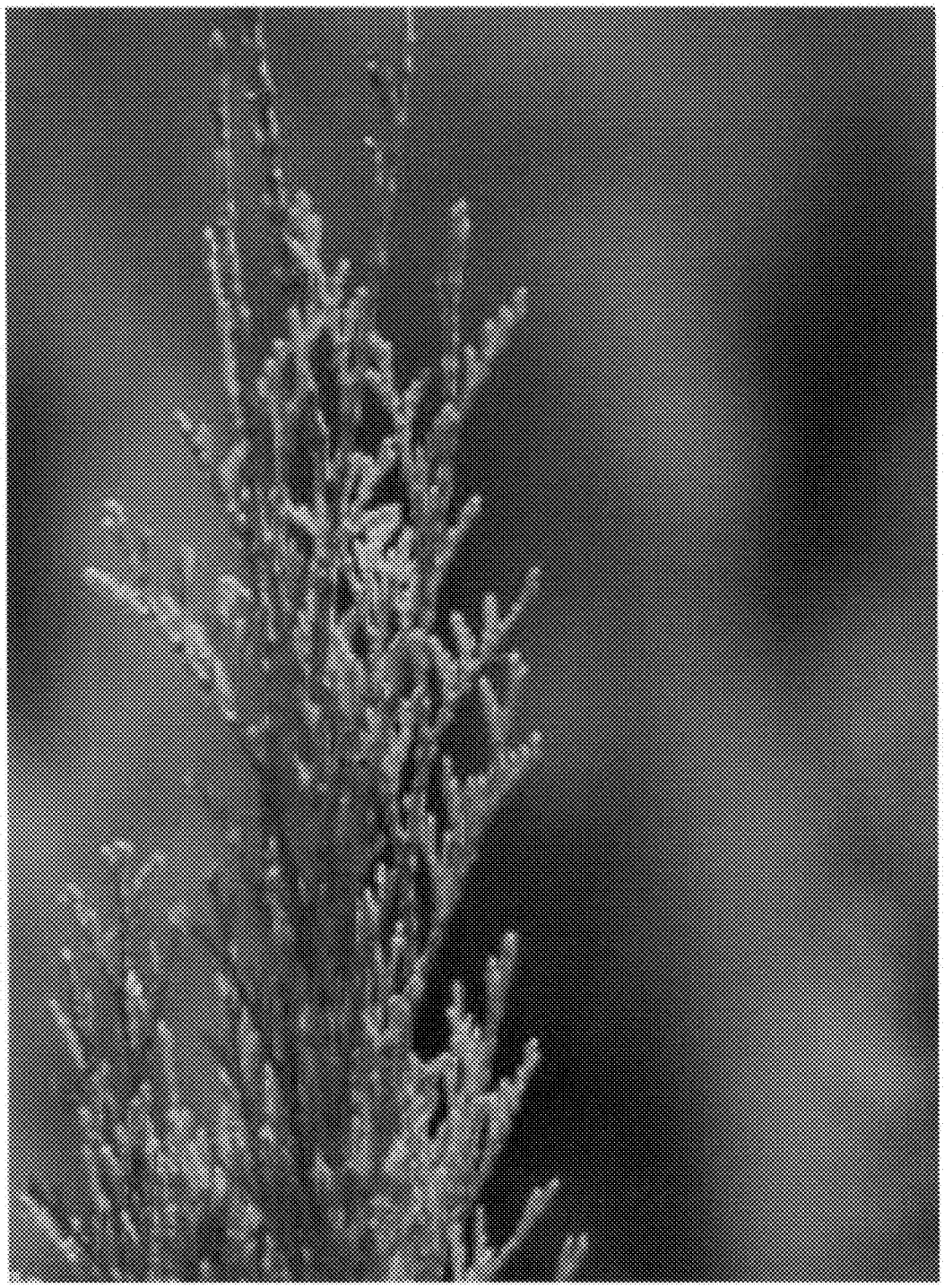

The drawing labeled as FIG. 3 depicts a close-up view of the foliage of 'JANED GOLD'. Drawings are made using conventional techniques and although foliage colors may appear different from actual colors due to light reflectance, they are as accurate as possible by conventional photography.

BOTANICAL DESCRIPTION OF THE PLANT

The following is a detailed description of 'JANED GOLD'. Color determinations are in accordance with The R.H.S. Colour Chart of The Royal Horticultural Society, London England except where general color terms of ordinary dictionary significance are used. Data was collected in Arroyo Grande, Calif. from a 2-year-old 1-liter container plant. Growing requirements are similar to the species.

Botanical classification: *THUJA occidentalis* 'JANED GOLD'.
Genus: *THUJA*.
Species: *occidentalis*.
Denomination: 'JANED GOLD'.
Family: Cupressaceae.
Common name: White cedar or Eastern arborvitae.
Type: Shrub.
Commercial classification: Ornamental.
Use: Hedge or accent plant for garden and landscape.
Parentage: *THUJA occidentalis* 'JANED GOLD' was discovered as a chance seedling that resulted from the parent, namely an individual *Thuja occidentalis* 'Smaragd' (unpatented).
Growth rate: Slow during first 3 years and afterward comparable to parent.
Plant dimensions (1-liter container): 25 cm. in height and 20 cm. in width.
Hardiness: USDA Zone 5.
Propagation: Hardwood cuttings.
Time to initiate rooting (average): 45 days at 18° Celsius air temperature.
Time to root cuttings (average): 150 days at 18° Celsius air temperature.
Time to produce a commercial crop (average): 2 years.
Vigor: Robust and vigorous.
Disease susceptibility or resistance: None known to the inventor.
Pest susceptibility or resistance: Bagworms and spider mites can be occasional pests.
Growth habit: Dense, uniform narrow upright.
Shape: Conical.
Special considerations: Tolerates clipping, survives boggy soils, wind resistant.
Trunk surface: Bark vertically stringy exfoliating in long strips.
Diameter of trunk: 1.50 cm. diameter.
Bark color: N200B.
Stem:
- *Branching habit.*—Horizontal to ascending.
- *Branch quantity* (*average*).—8 vertical branches per 1-liter container plant.
- *Branch color.*—N200B.
- *Branch surface.*—Scabrid.
- *Branch dimensions* (*average*).—20 cm. in length and 0.30 cm. in width.
- *Branchlet quantity* (*average*).—6 per vertical branch.
- *Branchlet shape.*—Flattened into fan-shaped sprays.
- *Branchlet color.*—144A nearest stem, becoming 151A at and close to the apex and at the margins.
- *Branchlet surface.*—Scale-like.
- *Branchlet dimensions* (*average*).—11 cm. in length and 6 cm. in width.
- *Internodes* (*range*).—1.0 cm-1.5 cm.

Foliage:
- *Leaf shape.*—Ovate.
- *Leaf form.*—Adpressed and scale-like.
- *Leaf arrangement.*—Opposite, with lateral leaves overlapping facial pair.
- *Leaf division.*—Simple.
- *Leaf margin.*—Entire.
- *Leaf apex.*—Cuspidate.
- *Leaf base.*—Truncate.
- *Leaf color* (*both surfaces*).—144 A nearest stem, becoming 151A at and close to the apex and at the margins.
- *Venation pattern.*—Inconspicuous.
- *Facial leaf dimensions* (*average*).—3 mm. in length and 2 mm. in width.
- *Lateral leaf dimensions* (*average*).—2 mm. in length and 1 mm. in width.
- *Leaf attachment.*—Sessile.
- *Leaf texture.*—Fleshy.
- *Leaf surface* (*abaxial surface*).—Glabrous.
- *Leaf surface* (*adaxial surface*).—Glabrous.
- *Leaf quantity* (*average per spray*).—> 200 in number.
- *Fragrance.*—Resinous scent when bruised.

Flowers (cones):
- *Arrangement.*—Monoecious.
- *Female flowers* (*solitary, borne at end of branchlets*).—Spherical, tiny, 1 mm-2 mm in diameter, chartreuse in color, except at time of pollination when color turns pink-red.
- *Male flowers.*—(Solitary, borne in axils of branchlets, adjacent to stem) ellipsoid, 10 mm in length, reddish-brown in color.
- *Scales* (*separating from cones as cones mature, remaining basally attached*).—4-6 pairs, leathery in texture, cinnamon brown in color, base cuneate, apex acute, hooked.
- *Seeds.*—Lenticular, 2-winged, 1-3 seeds per scale, color brown.

The invention claimed is:

1. A new and distinct variety of *THUJA* plant named 'JANED GOLD' substantiated by the descriptions and illustrations herein.

* * * * *